United States Patent [19]
Tornier et al.

[11] Patent Number: 5,879,395
[45] Date of Patent: Mar. 9, 1999

[54] TOTAL ELBOW PROSTHESIS

[75] Inventors: Alain Tornier, St. Ismier; Thierry Judet, Ville D'Avray, both of France

[73] Assignee: Tornier SA, Saint Ismier, France

[21] Appl. No.: 9,887

[22] Filed: Jan. 21, 1998

[30] Foreign Application Priority Data

Jan. 23, 1997 [FR] France .................................. 97 00909

[51] Int. Cl.⁶ ....................................................... A61F 2/38
[52] U.S. Cl. ............................................................. 623/20
[58] Field of Search .................. 623/20, 18, 16

[56] References Cited

U.S. PATENT DOCUMENTS

| | | |
|---|---|---|
| 4,242,758 | 1/1981 | Amis et al. . |
| 4,883,490 | 11/1989 | Oh ............................................. 623/22 |
| 4,892,548 | 1/1990 | Niederer et al. ......................... 623/22 |
| 5,782,923 | 7/1998 | Engelbrecht et al. ..................... 623/20 |

FOREIGN PATENT DOCUMENTS

| | | |
|---|---|---|
| 2403069 | 4/1979 | France . |
| 2663838 | 1/1992 | France . |
| 2720930 | 12/1995 | France . |
| 4331282 | 3/1995 | Germany . |
| 1 444 724 | 8/1976 | United Kingdom ..................... 623/18 |
| 2134360 | 8/1984 | United Kingdom . |

*Primary Examiner*—David H. Willse
*Attorney, Agent, or Firm*—Greenblum & Bernstein, P.L.C.

[57] ABSTRACT

A total elbow prosthesis includes a radial element having an anchoring stem provided with a neck which is inclined by an angle of between 0° and 30° relative to the axis of the anchoring stem. The neck is integral with a ball on which a cylindrical head articulates. The cylindrical articulating head includes an upper face of concave profile which cooperates with the epicondylar surface of the humeral element and a cylindrical circumference cooperating with an outer articular surface provided on the outer flank of a flange of the ulnar element.

7 Claims, 4 Drawing Sheets

TOTAL ELBOW PROSTHESIS

BACKGROUND OF THE INVENTION

1. Field of the Invention

The present invention relates to a total elbow prosthesis of the type comprising a first, humeral element, a second, ulnar element, and a third, radial element.

2. Description of Background Information

Prostheses of this type are known which include these three elements but in which the third, radial element is integral with its stem and fixed relative to the bone, preventing any possibility of freedom of rotation about its axes. In addition, this total elbow prosthesis is not designed to form the radio-ulnar articulation, that is to say between the radial element and the ulnar element.

Such prostheses have certain drawbacks, in particular risks of instability, pain and loosening.

SUMMARY OF THE INVENTION

The object of the total elbow prosthesis according to the present invention is to overcome these drawbacks by forming the articulation between the ulnar element and the radial element.

The elbow prosthesis according to the present invention comprises a radial element which includes means for forming the articulations with the radial articular surface of the humeral element and the outer articular surface of the ulnar element.

Moreover, the total elbow prosthesis includes a radial element equipped with an anchoring stem provided with a neck which is integral with a ball on which a cylindrical head articulates, the upper face of said cylindrical head having a concave profile which cooperates with the radial articular surface of the humeral element, while the cylindrical circumference of the head cooperates with the outer articular surface of the ulnar element.

BRIEF DESCRIPTION OF THE DRAWINGS

The description which follows with reference to the attached drawings, which are given by way of nonlimiting example, will permit a clearer understanding of the invention, of the characteristic features it presents, and of the advantages which it may afford.

DETAILED DESCRIPTION OF THE INVENTION

Figure 1:
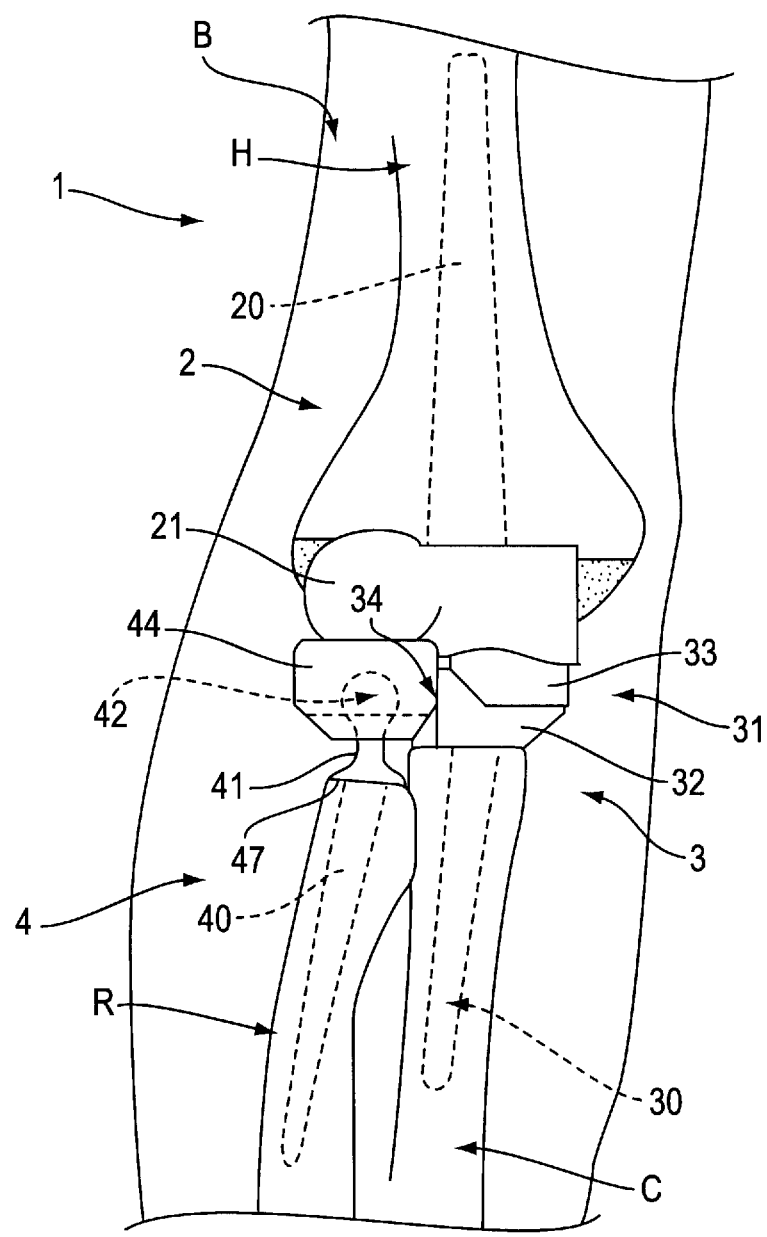
FIG. 1 is a view of a right arm representing the elbow prosthesis according to the invention in the anatomical frontal plane, with the arm stretched.
Figure 2:
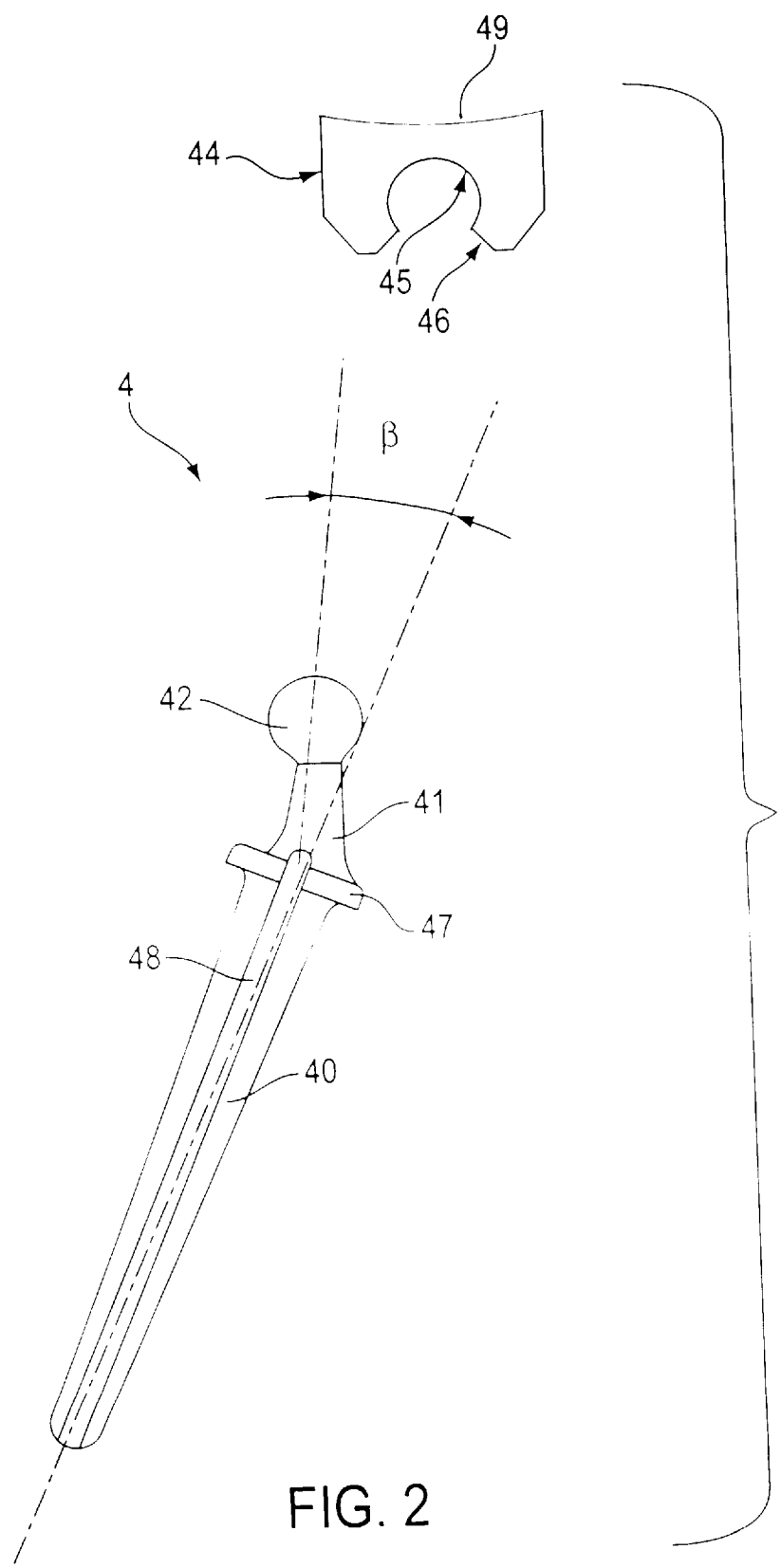
FIG. 2 is a view showing the radial element of the elbow prosthesis according to the present invention, equipped with its head which is made of plastic, for example.

A total elbow prosthesis 1 is represented in FIGS. 1 and 2 and is made up of a humeral element 2 intended for anchoring in the humerus H, an ulnar element 3 integral with the ulna C, and a radial element 4 fixed in the radius R of a right arm B.

The humeral element 1 comprises a metal articular part reproducing the anatomical articulation parts which are designed to come into contact with the radial head on the outer side and with the ulna on the inner side.

The humeral element includes an anchoring stem 20 integral with an epicondylar part 21 reproducing the articular surface of the humerus.

The ulnar element 3 comprises an anchoring stem 30 intended for anchoring in the ulna C, an articular surface 31 cooperating with the epicondylar part 21 of the humeral component 2.

The articular surface 31 is, for example, made up of a metal flange 32 integral with the stem 30, on which a plateau 33 made of polyethylene is fixed opposite the corresponding articular surface of the epicondylar part 21.

The metal flange 32 has, on its outer flank, in a plane substantially parallel to the axis of the stem 30 of the ulnar element 3, an articular surface 34 having a substantially concave profile.

The radial element 4 represented in FIGS. 1 and 2 has a stem 40 intended to anchor in the radius R and surmounted by a neck 41 integral with a ball 42 on which there engages an articular head 44 of generally cylindrical or conical shape.

The articular head 44 is pierced with a spherical seat 45 with a conical entrance 46 for receiving the ball 42.

The stem 40 is of generally cylindrical or conical shape and receives at its proximal part a shoulder 47 intended to bear on the radial osseous cutting. The stem 40 is in addition equipped with grooves 48 intended to facilitate the anchoring in the bone tissue or cement. The neck 41 is inclined relative to the axis of the stem 40 by an angle $\beta$ of between 0 and 30°.

The head 44 ends in a concave face 49 having a geometrical radius substantially equivalent to that of an anatomical radial head in order to cooperate with the radial portion of the epicondylar surface 21 of the humeral element 2.

It will be observed that the spherical seat 45 of the head 44 opens into the conical part 46 in order to afford a sufficient clearance for the articulation of the ball 42.

It will be noted that the spherical seat 45 can be made either to hold or not to hold the ball 42.

The articular head 44 has a cylindrical outer circumference cooperating with the articular surface 34 provided on the outer flank of the flange 32 of the ulnar element 3.

It will be noted that in the structure shown in FIGS. 1 and 2 the articular head 44 is made entirely of plastic. This head is completely free in its three degrees of freedom of rotation relative to the center of the ball 42. This configuration allows the articular head 44 to cooperate efficiently both with the epicondylar surface 21 of the humeral element 2 and with the articular surface 34 of the ulnar element 3, all along the movement of flexion of the forearm.

Figure 3:
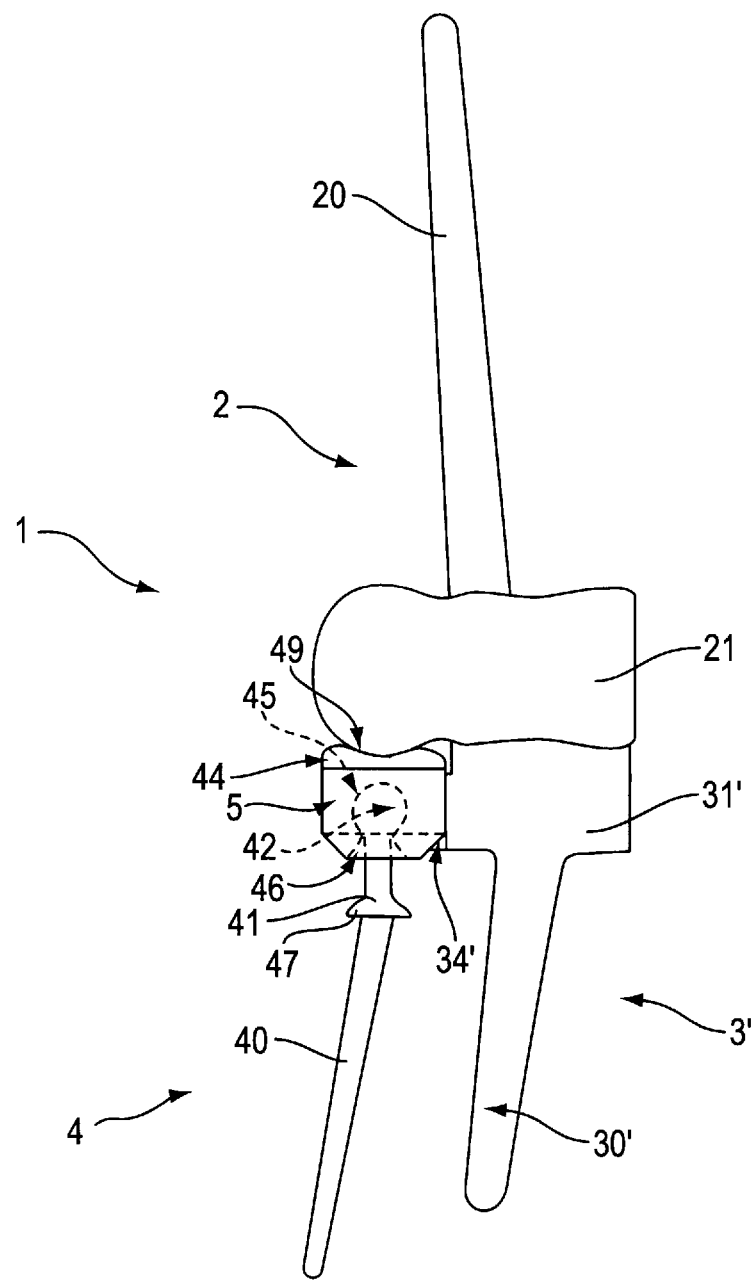
FIG. 3 is a view illustrating a first variant of the elbow prosthesis.

FIG. 3 shows a variant of the total elbow prosthesis 1 in which the radial head 44 receives a metal hoop 5 which is able to cooperate with the articular surface 34' of the ulnar element 3', then made of polyethylene. The ulnar element 3' made up of its stem 30' and of its articular surface 31' are in fact made completely of polyethylene.

It is also possible for the articular surface 31' made of polyethylene to be fixed on a metal flange integral with a stem which is also made of metal. In this case, the articular surface 31' also includes on its outer flank the articular surface 34' in order to form the radio-ulnar articulation.

Figure 4:
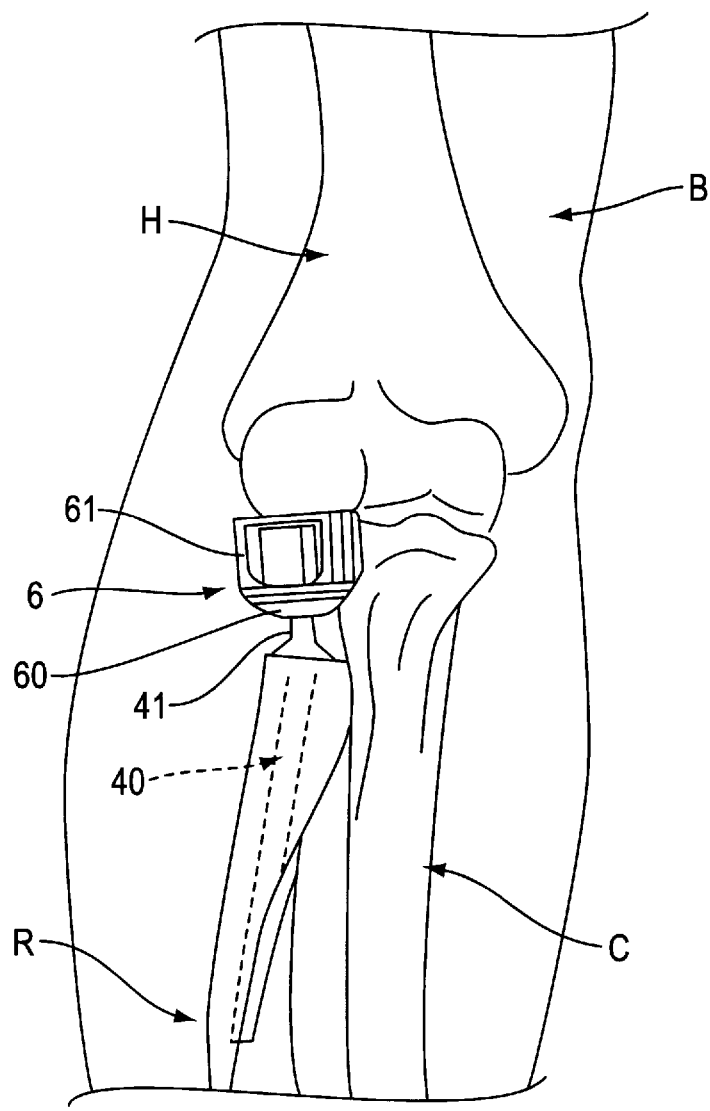
FIG. 4 is a view showing an elbow joint equipped solely with the radial element of the elbow prosthesis according to the present invention.

FIG. 4 shows a second variant of the elbow prosthesis 1 which consists in using only the radial element in an articulation which is otherwise healthy. Indeed, only the radial element is anchored in the radius R so that its articular head 6, in this case made up of a polyethylene body 60 enclosed by a metal cup 61 which cooperates both with the humeral and ulnar anatomical articular surfaces.

The metal cup 61 is provided to cover the cylindrical circumference of the body 60 but also the concave upper face which cooperates with the healthy humeral articulation.

Likewise, the body 60 has a spherical seat identical to that described previously, in order to receive the ball 42 integral with the neck 41 of the radial element 4.

It will be noted that the articular head 44 and the ball 42 of the radial element 4 can be made of any material, and more particularly of ceramic.

We claim:

1. Total elbow prostheses comprising a first, humeral element equipped with an epicondylar articular surface, a second, ulnar element provided with an articular surface, and a radial element, wherein the radial element includes an anchoring stem provided with a neck which is inclined by an angle $\beta$ of between 0° and 30° relative to an axis of said stem, said neck being integral with a ball on which a cylindrical head articulates, said cylindrical head including an upper face of concave profile which cooperates with the epicondylar surface of the humeral element, and a cylindrical circumference cooperating with an outer articular surface provided on an outer flank of a flange of the ulnar element (3).

2. Elbow prosthesis according to claim 1, wherein the head is provided with a metal hoop which cooperates with the articular surface of the ulnar element.

3. Elbow prosthesis of claim 2, wherein the ulnar element is polyethylene.

4. Elbow prosthesis according to claim 1, wherein the head includes a spherical seat provided with a conical part for receiving the ball in order to permit said head a sufficient angular clearance.

5. Elbow prosthesis according to claim 1, wherein the radial element includes the head which is provided with a polythylense body enclosed by a metal cup.

6. Elbow prosthesis according to claim 1, wherein the head is completely free in three degrees of rotation relative to a center of the ball.

7. Elbow prosthesis according to claim 1, wherein the head and the ball of the radial element are made of ceramic material.

* * * * *